United States Patent
Anklam et al.

(10) Patent No.: US 11,453,636 B2
(45) Date of Patent: Sep. 27, 2022

(54) PROCESS FOR SEPARATION AND PURIFICATION OF A DICARBOXYLIC ACID CONTAINING MIXTURE

(71) Applicant: Archer Daniels Midland Company, Decatur, IL (US)

(72) Inventors: Pam Anklam, Lovington, IL (US); William Chris Hoffman, Decatur, IL (US); Mitchell Schultz, Mt. Zion, IL (US); John G. Soper, Mt. Zion, IL (US)

(73) Assignee: ARCHER DANIELS MIDLAND COMPANY, Decatur, IL (US)

(*) Notice: Subject to any disclaimer, the term of this patent is extended or adjusted under 35 U.S.C. 154(b) by 364 days.

(21) Appl. No.: 16/623,535

(22) PCT Filed: Jun. 20, 2018

(86) PCT No.: PCT/US2018/038418
§ 371 (c)(1),
(2) Date: Dec. 17, 2019

(87) PCT Pub. No.: WO2018/236950
PCT Pub. Date: Dec. 27, 2018

(65) Prior Publication Data
US 2021/0147332 A1 May 20, 2021

Related U.S. Application Data

(60) Provisional application No. 62/523,540, filed on Jun. 22, 2017.

(51) Int. Cl.
*B01D 15/36* (2006.01)
*C07C 51/47* (2006.01)
*C07C 59/105* (2006.01)
*C07C 59/285* (2006.01)
*B01J 43/00* (2006.01)
*B01D 15/18* (2006.01)

(52) U.S. Cl.
CPC .......... *C07C 51/47* (2013.01); *B01D 15/364* (2013.01); *B01J 43/00* (2013.01); *C07C 59/105* (2013.01); *C07C 59/285* (2013.01); *B01D 15/1821* (2013.01); *B01D 2215/023* (2013.01)

(58) Field of Classification Search
CPC ..... C07C 51/47; C07C 59/105; C07C 59/285; B01D 15/1821; B01D 15/364; B01J 43/00
See application file for complete search history.

(56) References Cited

U.S. PATENT DOCUMENTS

| | | | |
|---|---|---|---|
| 6,884,345 B1* | 4/2005 | Irgum | B01J 20/289 502/402 |
| 2009/0107918 A1 | 4/2009 | Klipper et al. | |
| 2010/0320373 A1 | 12/2010 | Appelblad | |
| 2013/0158255 A1* | 6/2013 | Archer | C07C 51/412 564/468 |
| 2013/0345473 A1* | 12/2013 | Archer | C07C 51/47 562/580 |
| 2016/0090346 A1* | 3/2016 | Diamond | B01D 15/1821 562/580 |

FOREIGN PATENT DOCUMENTS

| | | | |
|---|---|---|---|
| JP | 2014-039505 | 3/2014 | |
| WO | WO-2017095686 A1 * | 6/2017 | B01J 15/36 |

OTHER PUBLICATIONS

Marrubini, G., et al., Column comparison and method development for the analysis of shor-chain carboxylic acids by zwitterionic hydrophilic interaction liquid chromatography with UV detection, J. Sep. Sci. vol. 36, pp. 3493-3502 (Year: 2013).*
Merck KGaA,, ZIC-pHILIC HPLC column, Merck scientific papers, 1 page (Year: 2003).*
Marrubini et al., 'col. comparison and method development for the analysis of short-chain carboxylic acids by zwitterionic hydrophilic interaction liquid chromatography with UV detection', Journal of Separation Science, vol. 36, Oct. 1, 2013 (Oct. 1, 2013), p. 3493-3502.

* cited by examiner

*Primary Examiner* — Yate' K Cutliff
(74) *Attorney, Agent, or Firm* — William B. Miller

(57) ABSTRACT

A method is provided for separating a dicarboxylic acid product from a mixture containing such dicarboxylic acids. The method involves: providing a dicarboxylic acid-containing mixture of which at least 35% of the carboxylic acid content of the mixture is a dicarboxylic acid product of interest; running an extraction of said dicarboxylic acid-containing mixture through a chromatographic column configured with an amphoteric resin, such that the dicarboxylic acid product elutes preferentially from the dicarboxylic acid-containing mixture. In certain embodiments, the dicarboxylic acid product of interest can be a glucaric or gluconic acid product from a mixture of either or both of these with still other carboxylic acids.

5 Claims, No Drawings

PROCESS FOR SEPARATION AND PURIFICATION OF A DICARBOXYLIC ACID CONTAINING MIXTURE

FIELD OF INVENTION

The present disclosure relates to chromatographic separation of organic compounds. In particular, the present invention pertains to a method for producing purified dicarboxylic acids from a dicarboxylic acid containing mixture, at least in part by chromatographic means.

BACKGROUND ART

Processes for the preparation of dicarboxylic acids are known to produce crude mixtures containing various on-path and off-path carboxylic acids. Various waste streams from other processes may also contain dicarboxylic acids of commercial interest.

Processes for the refining of these crude mixtures and waste streams are needed and have been developed to enable a sufficiently pure dicarboxylic acid product to be produced from the crude mixtures or provide useful fractions of waste streams containing dicarboxylic acids for further use or refining.

One dicarboxylic acid that has attracted recent commercial interest is glucaric acid. U.S. Pat. No. 9,776,945 to Diamond et al. describes methods for the recovery of dicarboxylic acids generally using anion exchange chromatography with particular eluents such as organic acids (e.g., acetic acid or formic acid), bases (e.g., sodium bicarbonate or sodium tetraborate), and strong acids (e.g., sulfuric or hydrochloric acid), but indicates that the use of such eluents other than water is undesirable for increasing reagent costs and requiring disposal or additional removal and recycling costs. In particular contemplation of processes for the oxidation of aqueous sugar solutions to produce the corresponding acids, for example, the oxidation of glucose to provide glucaric acid as described in U.S. Pat. No. 8,669,397 to Boussie et al. or of xylose to provide xylaric acid as described in U.S. Pat. No. 8,785,683, Diamond et al. thus propose contacting a separation media in a separation zone with the reaction product of Boussie et al., separating at least a portion of the glucaric acid or a salt thereof in the reaction product from other, on-path intermediates to the glucaric acid (especially gluconic acid, which is formed at comparable levels to glucaric acid in Boussie et al's process) which intermediates are contained in a raffinate, removing the raffinate from the separation zone, and eluting the glucaric acid or its salt from the separation media with an eluent comprising water.

A preferred separation media is described as comprising a weakly basic anion exchange chromatography resin employed in a simulated moving bed, especially a glucarate form of an anion exchange chromatography resin. Combinations of these resins with weak base and strong base functionalities are also described as useful. A particular example of a process for the separation of glucaric acid from gluconic acid and other on-path intermediates is given in Example 2, and involved a simulated moving bed system employing a Lanxess Lewatit MDS 4368 styrene/divinylbenzene cross-linked macroporous anion exchange resin (characterized as having 75-80% weak base and 25-20% strong base functionality) with 1.4 eq/L exchange capacity and 0.3 mm bead size. The free-base and hydroxyl forms of the resin were converted to the glucarate form by exposure to a 1M glucaric acid solution before use. Enrichment of the glucaric acid content was said to be enabled from 47.9 mol percent in the feed to 90.1 mol percent in the extract, with 97 percent by mass of unconverted glucose and on-path intermediates being concentrated in the raffinate and available for recycle back to the oxidation process of Boussie et al. to make additional glucaric acid.

SUMMARY OF THE INVENTION

The present disclosure describes a method for separating a dicarboxylic acid product from a mixture containing such dicarboxylic acids. The method involves: providing a dicarboxylic acid-containing mixture of which at least 35% of the carboxylic acid content of the mixture is a dicarboxylic acid product of interest; running an extraction of said dicarboxylic acid-containing mixture through a chromatographic column configured with an amphoteric resin, such that the dicarboxylic acid product elutes preferentially from the dicarboxylic acid-containing mixture. In certain embodiments, the dicarboxylic acid product of interest can be a glucaric or gluconic acid product from a mixture of either or both of these with still other carboxylic acids.

DETAILED DESCRIPTION OF EMBODIMENTS

As used in this application, the singular forms "a", "an" and "the" include plural references unless the context clearly indicates otherwise. The term "comprising" and its derivatives, as used herein, are similarly intended to be open ended terms that specify the presence of the stated features, elements, components, groups, integers, and/or steps, but do not exclude the presence of other unstated features, elements, components, groups, integers and/or steps. This understanding also applies to words having similar meanings, such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers, and/or steps. The term "consisting essentially of", as used herein, is intended to specify the presence of the stated features, elements, components, groups, integers, and/or steps, as well as those that do not materially affect the basic and novel characteristic(s) of stated features, elements, components, groups, integers, and/or steps. Terms of degree such as "substantially", "about" and "approximately" as used herein mean, regardless of the degree of precision conventionally understood by the number of significant figures used in numerically describing a particular attribute, plus or minus five (5) percent from a stated value.

Where specific numerical values are used to quantify certain parameters relating to the invention without an accompanying term of degree, and where the specific numerical values are not expressly part of a numerical range, it will be understood that each such specific numerical value provided herein is to be construed as providing literal support for a broad, intermediate and narrow range of values for the parameter in question. The broad range shall be the numerical value plus and minus 60 percent of the numerical value, rounded to two significant digits. The intermediate range shall be the numerical value plus and minus 30 percent of the numerical value, rounded to two significant digits, while the narrow range shall be the numerical value plus and minus 15 percent of the numerical value again to two significant digits. Further, these broad, intermediate and narrow numerical ranges should be applied not only to the specific values, but also to the differences between these specific values. Thus, if the specification describes a first pressure of 110 kPa for a first stream and a second pressure of 48 kPa (a difference of 62 kPa) for a second stream, the broad, intermediate and narrow ranges for the pressure difference between these two streams would be 25 to 99 kPa, 43 to 81 kPa, and 53 to 71 kPa, respectively.

Where the present description uses numerical ranges to quantify certain parameters relating to the invention, it will be similarly understood that these ranges are to be construed as providing literal support for claim limitations that only recite the lower value of the range as well as claim limitations that only recite the upper value of the range.

Unless otherwise indicated, any definitions or embodiments described in this or in other sections are intended to be applicable to all embodiments and aspects of the subjects herein described for which they would be suitable according to the understanding of a person of ordinary skill in the art.

Amphoteric resins contain both positive and negative functional groups attached to a polystyrene matrix. These kinds of resins are typically used for the separation of an electrolyte and non-electrolyte or for the separation of two different electrolytes (e.g., sugar/salt, glycerin/salt, caustic material/salt, salt/salt). Positive cations and negative anions of materials or compounds of interest selectively bind to the corresponding portion of the amphoteric resin.

In the context of the present invention, amphoteric resins containing both weakly acidic positive and strongly basic negative functional groups attached to a polystyrene matrix have proven particularly well-suited to the recovery of glucaric acid from a mixture of glucaric acid with other carboxylic acids generally and other dicarboxylic acids specifically, for example, but without limitation, as generated by a manufacturing process as described in U.S. Pat. No. 8,669,397 to Boussie et al. In one embodiment, such resins are used in simulated moving bed chromatography.

D-glucaric acid (also known as saccharic acid) is commercially available and produced by the nonselective chemical oxidation of glucose, using nitric acid as the oxidant, though other methods have been proposed for producing glucaric acid-containing mixtures within the scope of the present invention, wherein glucaric acid is at least 35 percent of the total carboxylic acid content of the mixture, and would be preferred. Parenthetically, for clarity, a "glucaric acid-containing mixture" according to the present invention may comprise glucaric and other carboxylic acids per se, or may comprise salts of glucaric and other carboxylic acids in which the glucarate salt content of the mixture is at least 35 percent of the total carboxylate salt content of the mixture.

As related in U.S. Pat. No. 8,669,397 to Boussie et al., U.S. Pat. No. 2,472,168 illustrates a method for the preparation of glucaric acid from glucose using a platinum catalyst in the presence of oxygen and a base. Further similar examples of the preparation of glucaric acid using a platinum catalyst in the presence of oxygen and a base may be found in the *Journal of Catalysis*, vol. 67, pp. 1-13 and 14-20 (1981). Other prior oxidation methods referenced by Boussie et al. include those described in U.S. Pat. No. 6,049,004 (use of solvent extraction with dialkyl ether to crystallize glucaric acid following nitric acid oxidation, and avoid necessity of neutralization); U.S. Pat. No. 5,599,977 (nitric acid oxidation with gas injection into reaction product for moderating temperature increases, followed by neutralization); U.S. Pat. No. 6,498,269 (use of an oxoammonium catalyst/halide co-catalyst system); *J. Chem. Technol. Biotechnol.*, vol. 76, pp. 186-190 (2001) (D-glucaric acid by oxidation of molasses in packed beds using vanadium pentoxide catalyst with nitric acid in oxidizing medium); *J. Agr. Food Chem.*, vol. 1, pp. 779-783 (1953); *J. Carbohydrate Chem.*, vol. 21, pp. 65-77 (2002)(4-AcNH-TEMPO-catalyzed oxidation of D-glucose to D-glucaric acid using elemental chlorine or bromine as the terminal oxidant); *Carbohydrate Res.*, vol. 337, pp. 1059-1063 (2002) (TEMPO-mediated oxidation of glucose to glucaric acid using bleach). However, these processes are characterized by Boussie et al. as suffering from various economic shortcomings resulting from, among other issues, process yield limitations and the requirement for additional reaction constituents.

Against the background of these prior published oxidation methods, U.S. Pat. No. 8,669,397 to Boussie et al. describes a catalytic method for producing glucaric acid from glucose, with the glucaric acid then being converted by hydrodeoxygenation to adipic acid. According to Boussie et al., glucose can be converted to glucaric acid in high yield by reacting glucose with oxygen (in the form of air, oxygen-enriched air or oxygen with other constituents substantially inert to the reaction) in the presence of a catalyst typically including one or more of palladium and platinum optionally in the presence of one or more other d-block metals (e.g., Rh or Ru), alone or in combination with one or more rare earth metals, alone or in combination with one or more main group metals (e.g., Al, Ga, Tl, In, Sn, Pb or Bi) on a support or unsupported, but in the absence of added base.

Processes for separating the glucaric acid from other components of the reaction product from Boussie et al's oxidation process are described in US 2016/0090346 to Diamond et al, as already summarized above.

For purposes of the present invention, the method described in Boussie et al. is preferred to the other oxidation methods described for making glucaric acid from glucose, though we would propose an alternative method to that of Diamond et al. for separating the glucaric and gluconic acids in a mixture of these acids.

Our improved separation step would involve chromatographic separation by means of an amphoteric resin rather than a weakly basic anion exchange resin, preferably in a simulated moving bed system. Examples are given below for demonstrating the surprising effectiveness of such resins for separating these carboxylic acids of generally very similar properties.

A preferred method for separating glucaric acid from gluconic acid in a mixture such as produced by Boussie et al. according to our conception would however involve providing a glucaric acid-containing mixture of which at least 35% of the carboxylic acid content of the mixture (in certain embodiments, for example, being 40%-55% of the carboxylic acid content) is glucaric acid; running an extraction of the mixture through a chromatographic column configured with an amphoteric resin, such that the desired glucaric acid feed material elutes preferentially from the mixture. We have surprisingly found that an amphoteric resin provided a preferential affinity ratio of at least 2:1 to 3:1 for glucarate:gluconate, indicating superior separation potential to the weakly basic anion exchange resins taught by Diamond et al., with improved performance of the amphoteric resin over time as well compared to a weakly basic anion exchange resin.

Example 1 and Comparative Example 1

For demonstrating the manner in which a glucaric acid could be recovered from a product as produced by Boussie et al., a series of pulse tests were run using an aqueous feed mixture containing 6.3% by weight of gluconate salts, 8.2% by weight of glucarate salts, 0.013% of chloride, 0.025% of sulfate, and 2.7% of other organic acid salts (dry solids loading). More particularly, the breakdown of the aqueous feed mixture's various carboxylic acids by percentages of each was as follows: fumaric, 0.4; glycolic, 1.6; galacturonic, 7.7; 2-keto-gluconate, 0.4; 5-keto-gluconic, 3.3; glucuronic, 0.5; gluconic, 35.7, glucaric, 50.3 (total 100.0).

280 mL of the particular Lanxess Lewatit MDS 4368 styrene/divinylbenzene cross-linked macroporous anion exchange resin exemplified in Diamond et al. was loaded for comparison into 2 jacketed glass columns (25 mm×600 mm) and the air bubbles were removed. Both columns were connected to a water bath and heated to 50 degrees Celsius. The columns were rinsed with approximately 10 bed volumes of deionized water, then a first column (column #1) was conditioned with 7 bed volumes of the aqueous feed mixture while a second column (column #2) was conditioned with 7 bed volumes of a prepared saccharic acid solution which had been passed through 400 ml of Dowex 88 sodium form, macroporous strong acid cation exchange resin. Both columns were run upflow during the pretreatment due to swelling of the resin (about 40 percent swelling was observed). After pretreatment, the columns were then rinsed with 10 bed volumes of deionized water.

After the columns were conditioned in this manner, the columns were configured for down flow operation. The valve on top of the column was opened, then as the liquid level came even with the top of the resin bed a pulse of 20 milliliters of the aqueous feed mixture was introduced. As the liquid level drew even again with the top of the resin bed, 1-2 milliliters of DI water were added and the valve at the top of the column was closed. An elution flow of 20 milliliters per minute of DI water was begun, and 34 fractions of about 48 mL each were collected at 0.16 bed volume intervals for subsequent analysis.

Subsequently, 280 mL of Mitsubishi DIAION AMP-03 amphoteric ion exchange resin, characterized by Mitsubishi as an amphoteric ion exchange resin in which a quaternary ammonium group and a carboxyl group are incorporated on a cross-linked polystyrene frame, as having a uniform bead size of 260 µm and outstanding resistance to degradation and leaching, were slurried in DI water and loaded into two of the same jacketed glass columns in the same manner as for the weakly basic anion exchange resin Lewatit MDS 4368. A first column was conditioned/pretreated using the same aqueous feed mixture, while the second column was conditioned/pretreated with deionized water. Pretreatment was accomplished in a down flow configuration for the amphoteric resin columns, however, as no swelling was expected and none was in fact observed. After rinsing with deionized water as before, pulse testing was undertaken with the aqueous feed mixture in the same manner as with the MDS 4368 resin.

Analysis of the fractions collected from the elution of the MDS 4368 columns and of the AMP-03 columns, respectively, demonstrates by comparing the cumulative areas of overlap of the gluconic acid or glucaric acid fractions, as the case may be, with the fractions for all other materials on the one hand and for glucaric acid and gluconic acid specifically and respectively from among the "all other materials" on the other hand, that the amphoteric resin provided superior performance to the weakly basic anion exchange resin offered by Diamond et al., see Table 1 below. More particularly, the amphoteric resin proved a much more effective resin for isolating the glucaric acid from a product mixture of the type described in Boussie et al., as compared to the weakly basic anion exchange resin advocated by Diamond et al. In Table 1, "OAGnF" will be understood as referring to the overlapping area of the gluconic acid fraction with "all other materials" and with glucaric acid specifically from among the "all other materials", and "OAGrF" correspondingly will be understood as referring to the overlapping area of the glucaric acid fraction with "all other materials" and with gluconic acid specifically from among the "all other materials":

TABLE 1

Relative Areas of Overlap Between MDS 4368 and AMP-03 Pulse Tests

| | AMP-03 Resin Pulse Test Results | | MDS 4368 Resin Pulse Tests | |
| --- | --- | --- | --- | --- |
| | Glucaric/ Others | Glucaric/ Gluconic | Glucaric/ Others | Glucaric/ Gluconic |
| OAGnF | 22.2 | 16.2 | 43.6 | 23.4 |
| OAGrF | 31.4 | 28.2 | 53.8 | 32.6 |

Example 2

A series of additional pulse tests were run using the same aqueous feed mixture as employed for Example 1 and Comparative Example 1, thus containing 6.3% by weight of gluconate salts, 8.2% by weight of glucarate salts, 0.013% of chloride, 0.025% of sulfate, and 2.7% of other organic acid salts (dry solids loading). More particularly, the breakdown of the aqueous feed mixture's various carboxylic acids by percentages of each was as follows: fumaric, 0.4; glycolic, 1.6; galacturonic, 7.7; 2-keto-gluconate, 0.4; 5-keto-gluconic, 3.3; glucuronic, 0.5; gluconic, 35.7, glucaric, 50.3 (total 100.0).

280 mL of Purolite® WCA100 amphoteric resin, having quaternary ammonium and carboxyl functionalities incorporated on a divinyl benzene-crosslinked gel polystyrene, was slurried with DI water and loaded into 2 jacketed glass columns (25 mm×600 mm) and the air bubbles removed, as done in Example 1 and Comparative Example 1. Both columns were connected to a water bath and heated to 50 degrees Celsius. The columns were rinsed with approximately 10 bed volumes of deionized water, then a first column (column #1) was conditioned with 7 bed volumes of the aqueous feed mixture while a second column (column #2) was conditioned with 7 bed volumes of deionized water as was done with the AMP-03 resin. After pretreatment, the columns were then rinsed with 10 bed volumes of deionized water.

After the columns were conditioned in this manner, the columns were configured for down flow operation. The valve on top of the column was opened, then as the liquid level came even with the top of the resin bed a pulse of 20 milliliters of the aqueous feed mixture was introduced. As the liquid level drew even again with the top of the resin bed, 1-2 milliliters of DI water were added and the valve at the top of the column was closed. An elution flow of 20 milliliters per minute of DI water was begun, and 34 fractions of about 48 mL each were collected at 0.16 bed volume intervals for subsequent analysis.

Overlapping area analysis of the fractions demonstrated that the WCA100 amphoteric resin likewise provided superior performance to the weakly basic anion exchange resin offered by Diamond et al. and essentially similar performance to the AMP-03 resin.

Examples 3-5

Pulse tests were conducted using the same apparatus and method as used in Example 1, but with only the amphoteric resin and with aqueous glucaric acid-containing feeds into which citric, malic and lactic acids were spiked in turn with larger amounts than they are found in a product mixture as produced by Boussie et al (U.S. Pat. No. 8,669,397).

More particularly, the breakdown of the various carboxylic acids by percentages of each was as follows, in each of the citric-, malic- and lactic-spiked aqueous glucaric acid-containing feeds for the pulse testing:

Citric-spiked—0.6 gluconate; 0.0 lactate; 0.04 glycolate; 0.09 2-keto-gluconate; 0.20 galacturonate/guluronate; 0.08 glucuronate; 0.19 5-keto-gluconate; 69.8 glucarate; 0.0 malate; 29.0 citrate.

Malic-spiked—0.6 gluconate; 0.0 lactate; 0.05 glycolate; 0.10 2-keto-gluconate; 0.22 galacturonate/guluronate; 0.11 glucuronate; 0.20 5-keto-gluconate; 67.4 glucarate; 31.3 malate; 0.03 citrate.

Lactic-spiked—0.51 gluconate; 25.6 lactate; 0.04 glycolate; 0.09 2-keto-gluconate; 0.21 galacturonate/guluronate; 0.09 glucuronate; 0.19 5-keto-gluconate; 73.3 glucarate; 0.0 malate; 0.03 citrate.

The results of the testing confirmed an ability to effectively separate glucaric acid from each of these other carboxylic acids, and indicate an elution order (from earliest to latest) as follows: gluconic, lactic, glucaric, malic and then citric acid. Based upon the compound structures and elution order, it would appear that the mechanism for adsorption onto the AMP-03 resin is an affinity for the double-bonded oxygen contained in these molecules. Gluconic acid and lactic acid both have a single double bonded oxygen, so the resin has less affinity for them and they elute earliest, while glucaric and malic both have two double bonded oxygens and elute closely together somewhat later, while citric acid contains three double bonded oxygens and elutes last of those tested. Based on these results, it is to be expected that ascorbic acid and acetic acid would elute earlier than glucaric acid and would also be separable from glucaric, while succinic and oxalic acid would elute similarly to malic and glucaric acids.

We claim:

1. A method for separation of a carboxylic acid of interest from a mixture containing this carboxylic acid among other carboxylic acids, comprising:

providing a carboxylic acid-containing mixture containing at least 35 wt. % of said carboxylic acid of interest based on the total carboxylic acid content of the mixture;

and running an extraction of said carboxylic acid-containing mixture through a chromatographic column configured with an amphoteric resin, such that the carboxylic acid product elutes from the carboxylic acid-containing mixture, wherein said carboxylic acid of interest is glucaric acid or gluconic acid and the mixture is a mixture of either or both of these with still other carboxylic acids; and said amphoteric resin has a surface characterized as having both weakly acidic positive and strongly basic negative functional groups on a polymeric backbone.

2. The method according to claim 1, applied to separate glucaric and gluconic acids from a mixture containing both glucaric and gluconic acids and in which at least one of these is present at greater than 35% by weight based on the total carboxylic acid content of the mixture.

3. The method according to claim 2, wherein glucaric acid or gluconic acid is present at a 50 wt. % or greater concentration in the mixture.

4. The method according to claim 3, wherein glucaric acid or gluconic acid is present at a 60 wt. % or greater concentration in the mixture.

5. The method according to claim 4, wherein glucaric acid or gluconic acid is present at a 70 wt. % or greater concentration in the mixture.

* * * * *